(12) United States Patent
Doyon

(10) Patent No.: US 8,772,008 B2
(45) Date of Patent: *Jul. 8, 2014

(54) METHODS AND COMPOSITIONS FOR INCREASING NUCLEASE ACTIVITY

(75) Inventor: Yannick Doyon, El Cerrito, CA (US)

(73) Assignee: Sangamo BioSciences, Inc., Richmond, CA (US)

( * ) Notice: Subject to any disclaimer, the term of this patent is extended or adjusted under 35 U.S.C. 154(b) by 203 days.

This patent is subject to a terminal disclaimer.

(21) Appl. No.: 12/800,599

(22) Filed: May 18, 2010

(65) Prior Publication Data

US 2011/0129898 A1 Jun. 2, 2011

Related U.S. Application Data

(60) Provisional application No. 61/216,526, filed on May 18, 2009.

(51) Int. Cl.
- *C12N 9/16* (2006.01)
- *C12N 5/07* (2010.01)
- *C07H 21/02* (2006.01)

(52) U.S. Cl.
USPC .......................... 435/196; 435/471; 536/23.1

(58) Field of Classification Search
None
See application file for complete search history.

(56) References Cited

U.S. PATENT DOCUMENTS

| | | |
|---|---|---|
| 5,356,802 A | 10/1994 | Chandrasegaran |
| 5,420,032 A | 5/1995 | Marshall et al. |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas et al. |
| 6,200,759 B1 | 3/2001 | Dove et al. |
| 6,242,568 B1 | 6/2001 | Barbas et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,528,313 B1 | 3/2003 | Le Mouellic et al. |
| 6,534,261 B1 | 3/2003 | Cox et al. |
| 6,607,882 B1 | 8/2003 | Cox et al. |
| 6,824,978 B1 | 11/2004 | Cox et al. |

(Continued)

FOREIGN PATENT DOCUMENTS

| | | |
|---|---|---|
| GB | 2338237 A | 12/1999 |
| WO | WO 95/19431 A1 | 7/1995 |

(Continued)

OTHER PUBLICATIONS

Qiu et al., *Saccharomyces cerevisiae* RNase H (35) functions in RNA primer removal during lagging-strand DNA synthesis, most efficiently in cooperation with Rad27 nuclease., Mol. Cell. Biol. (1999), vol. 19(12), pp. 8361-8371.*

(Continued)

*Primary Examiner* — Alexander Kim
(74) *Attorney, Agent, or Firm* — Pasternak Patent Law; Susan Abrahamson

(57) ABSTRACT

Methods and compositions for increasing nuclease activity by subjecting cells expressing the nuclease to hypothermic conditions to increase activity of the nucleases for genomic modifications.

4 Claims, 5 Drawing Sheets

(56) References Cited

U.S. PATENT DOCUMENTS

| | | | |
|---|---|---|---|
| 6,833,252 | B1 | 12/2004 | Dujon et al. |
| 6,903,185 | B2 | 6/2005 | Kim et al. |
| 6,933,113 | B2 | 8/2005 | Case et al. |
| 6,979,539 | B2 | 12/2005 | Cox et al. |
| 7,013,219 | B2 | 3/2006 | Case et al. |
| 7,153,949 | B2 | 12/2006 | Kim et al. |
| 7,163,824 | B2 | 1/2007 | Cox et al. |
| 2003/0232410 | A1 | 12/2003 | Liljedahl et al. |
| 2004/0002092 | A1 | 1/2004 | Arnould et al. |
| 2005/0026157 | A1 | 2/2005 | Baltimore et al. |
| 2005/0064474 | A1 | 3/2005 | Urnov et al. |
| 2005/0208489 | A1 | 9/2005 | Carroll et al. |
| 2006/0063231 | A1 | 3/2006 | Li et al. |
| 2006/0078552 | A1 | 4/2006 | Arnould et al. |
| 2006/0153826 | A1 | 7/2006 | Arnould et al. |
| 2006/0188987 | A1 | 8/2006 | Guschan et al. |
| 2006/0206949 | A1 | 9/2006 | Arnould et al. |
| 2007/0117128 | A1 | 5/2007 | Smith et al. |
| 2007/0218528 | A1 | 9/2007 | Miller |
| 2008/0131962 | A1 | 6/2008 | Miller |
| 2008/0159996 | A1 | 7/2008 | Ando et al. |
| 2008/0188000 | A1 | 8/2008 | Reik et al. |
| 2008/0299580 | A1 | 12/2008 | DeKelver et al. |
| 2009/0068164 | A1 | 3/2009 | Segal et al. |
| 2009/0117617 | A1 | 5/2009 | Holmes et al. |

FOREIGN PATENT DOCUMENTS

| | | |
|---|---|---|
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/16536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 2007/014275 A2 | 1/2007 |
| WO | WO 2007/139898 A2 | 12/2007 |
| WO | WO 2009/042163 A2 | 4/2009 |

OTHER PUBLICATIONS

Takeuchi et al. (Optimization of in vivo activity of a bifunctional homing endonuclease and maturase reverses evolutionary degradation., Nucleic Acids Research, (Epub Dec. 22, 2008), vol. 37, pp. 877-890.*
Invitrogen DH12S cells (2006).*
I-CreI DNA endonuclease (last viewed on Jan. 25, 2013).*
Yeast Protocols Handbook (2009).*
Guo et al., Protein tolerance to random amino acid change, 2004, Proc. Natl. Acad. Sci. Usa 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
Marco et al., A step ahead: combining protein purification and correct folding selection., Microb Cell Fact. (2004), vol. 3:12, pp. 1-3.*
Gasser et al., Protein folding and conformational stress in microbial cells producing recombinant proteins: a host comparative overview. Micriobial Cell Factories, (2008), vol. 7:11, pp. 1-18.*
Alwin et al., Custom Zinc-Finger Nucleases for Use in Human Cells., Molecular Therapy (2005), vol. 12, pp. 610-617.*

Methods in Molecular Biology (2008), Chromosomal Mutagenesis, Edited by Gregory D. Davis and Kevin J. Kayser, pp. 1-235.*
Wright et al. (Standardized reagents and protocols for engineering zinc finger nucleases by modular assembly., Nature Protocols (2006), vol. 1, pp. 1637-1652.*
Gateway Technology (2003).*
Kumar et al., Proliferation control strategies to improve productivity and survival during CHO based production culture., Cytotechnology (2007), vol. 53, pp. 33-46.*
Underhill et al., The cold-shock response in mammalian cells: investigating the HeLa cell cold-shock proteome., Cytotechnology (Apr. 2007), vol. 53(1-3), pp. 47-53.*
Argast, et al., "I-PpoI and I-CreI Homing Site Sequence Degeneracy Determined by Random Mutagenesis and Sequential In Vitro Enrichment," *J. Mol. Biol.* 280:345-353 (1998).
Arnould, et al., "Engineering of Large Numbers of Highly Specific Homing Endonucleases That Induce Recombination on Novel DNA Targets," *J Mol Biol* 355:443-458 (2006).
Ashworth, et al., "Computational Redesign of Endonuclease DNA Binding and Cleavage Specificity," *Nature* 441:656-659 (2006).
Beerli, et al., "Engineering Polydactyl Zinc-Finger Transcription Factors," *Nature Biotechnology* 20:135-141 (2002).
Belfort, et al., "Homing Endonucleases: Keeping the House in Order," *Nucleic Acids Research* 25:3379-3388 (1997).
Bitinate, et al., "FokI Dimerization Is Required for DNA Cleavage," *PNAS USA* 95:10570-10575 (1998).
Chames, et al., "In Vivo Selection of Engineered Homing Endonucleases Using Double-Strand Break Induced Homologous Recombination," *Nuc Acids Res* 33:e178(2005).
Chevalier, et al., "Design, Activity, and Structure of a Highly Specific Artificial Endonuclease," *Molecular Cell* 10:895-905 (2002).
Chilton, et al., "Targeted Integration of T-DNA Into the Tobacco Genome at Double-Stranded Breaks: New Insights on the Mechanism of T-DNA Integration," *Plant Physiology* 133:956-965 (2003).
Choo, et al., "Advances in Zinc Finger Engineering," *Curr. Opin. Struct. Biol.* 10:411-416 (2000).
Dujon, et al., "Mobile Introns: Definition of Terms and Recommended Nomenclature," *Gene* 82:115-118 (1989).
Epinat, et al., "A Novel Engineered Meganuclease Induces Homologous Recombination in Yeast and Mammalian Cells," *Nucleic Acids Research* 31:2952-2962 (2003).
Gimble, et al., "Substrate Recognition and Induced DNA Distortion by the PI-SceI Endonuclease, An Enzyme Generated by Protein Splicing," *J. Mol. Biol.* 263:163-180 (1996).
Gouble, et al., "Efficient In Toto Targeted Recombination in Mouse Liver by Meganuclease-induced Double-Strand Break," *J Gene Med* 8:616-622 (2006).
Isalan et al., "A Rapid, Generally Applicable Method to Engineer Zinc Fingers Illustrated by Targeting the HIV-1 Promoter," *Nat Biotechnol* 19:656-660 (2001).
Jasin, et al., "Genetic Manipulation of Genomes With Rare-Cutting Endonucleases," *Trends Genet* 12:224-228 (1996).
Kim, et al., "Chimeric Restriction Endonuclease," *PNAS USA* 91:883-887 (1994).
Kim, et al., "Insertion and Deletion Mutants of FokI Restriction Endonuclease," *J. Biol. Chem.* 269:31978-31981 (1994).
Kim, et al., "Getting a Handhold on DNA: Design of Poly-Zinc Finger Proteins With Femtomolar Dissociation Constents," *PNAS USA* 93:1156-1160 (1996).
Kita, et al., "The FokI Restriction-Modification System. I. Organization and Nucleotide Sequences of the Restriction and Modification Genes," *J Biol Chem* 264:5751-5765 (1989).
Li, et al., "Functional Domains in Fok I Restriction Endonuclease," *PNAS USA* 89:4275-4279 (1992).
Li, et al., "Alteration of the Cleavage Distance of Fok I Restriction Endonuclease by Insertion Mutagenesis," *PNAS USA* 90:2764-2768 (1993).
Lombardo, et al., "Gene Editing in Human Stem Cells Using Zinc Finger Nucleases and Integrase-Defective Lentniral Vector Delivery," *Nature Biotechnology* 25:1298-1306 (2007).
Miller, et al., "An Improved Zinc-Finger Nuclease Architecture for Highly Specific Genome Editing," *Nature Biotech* 25:778-785 (2007).

(56) References Cited

OTHER PUBLICATIONS

Monnat, et al., "Generation of Highly Site-Specific DNA Double-Strand Breaks in Human Cells by the Homing Endonucleases I-PpoI and I-CreI," *Biochem Biophysics Res Common* 255:88-93 (1999).

Pabo, et al., "Design and Selection of Novel Cys2-His2 Zinc Finger Proteins," *Ann. Rev. Biochem.* 70:313-340 (2001).

Paques, et al., "Meganucleases and DNA Double-Strand Break-Induced Recombination: Perspectives for Gene Therapy," *Current Gene Therapy* 7:49-66 (2007).

Perez, et al., "Establishment of HIV-1 Resistance in CD4+ T Cells by Genome Editing Using Zinc-Finger Nucleases," *Nature Biotechnology* 26:808-816 (2008).

Perler, et al., "Protein Splicing Elements: Inteins and Exteins A Definition of Terms and Recommended Nomenclature," *Nucleic Acids Research* 22:1125-1127 (1994).

Porteus, et al., "Gene Targeting Using Zinc Finger Nucleases," *Nature Biotechnology* 23:967-973 (2005).

Puchta, et al., "Two Different But Related Mechanisms Are Used in Plants for the Repair of Genomic Double-Strand Breaks by Homologous Recombination," *PNAS USA* 93:5055-5060 (1996).

Roobol, et al., "Biochemical Insights Into the Mechanisms Central to the Response of Mammalian Cells to Cold Stress and Subsequent Rewarming," *FEBS J* 276:286-302 (2009).

Roberts, et al., "Rebase: Restriction Enzymes and Methyltransferases," *Nucleic Acids Research* 31:418-420 (2003).

Rong, et al., "Targeted Mutagenesis by Homologous Recombination in *D. melanogaster*," *Genes & Dev* 16:1568-1581 (2002).

Rouet, et al., "Introduction of Double-Strand Breaks Into the Genome of Mouse Cells by Expression of a Rare-Cutting Endonuclease," *Molecular and Cellular Biology* 14:8096-8106 (1994).

Segal, et al., "Custom DNA-Binding Proteins Come of Age: Polydactyl Zinc-Finger Proteins," *Curr. Opin. Biotechnol.* 12:632-637 (2001).

Sussman, et al., "Isolation and Characterization of New Homing Endonuclease Specificities at Individual Target Site Positions," *J Mol Biol* 342:31-41 (2004).

Umov, et al., "Highly Efficient Endogenous Human Gene Correction Using Designed Zinc-Finger Nucleases" *Nature* 435:646-651 (2005).

U.S. Appl. No. 61/337,769, filed Feb. 8, 2010 entitled "Engineered Cleavage Half-Domains" by Doyon et al.

U.S. Appl. No. 61/395,836, filed May 17, 2010 entitled "Novel DNA-Binding Proteins and Uses Thereof" by Gregory et al.

* cited by examiner

METHODS AND COMPOSITIONS FOR INCREASING NUCLEASE ACTIVITY

CROSS-REFERENCE TO RELATED APPLICATIONS

The present application claims the benefit of U.S. Provisional Application No. 61/216,526, filed May 18, 2009, the disclosure of which is hereby incorporated by reference in its entirety.

STATEMENT OF RIGHTS TO INVENTIONS MADE UNDER FEDERALLY SPONSORED RESEARCH

Not applicable.

TECHNICAL FIELD

The present disclosure is in the field of genome engineering, particularly increasing nuclease activity.

BACKGROUND

Nucleases, including zinc finger nucleases and homing endonucleases such as I-SceI, that are engineered to specifically bind to target sites have been shown to be useful in genome engineering in basic research and in the pharmaceutical and biotechnology applications. For example, zinc finger nucleases (ZFNs) are proteins comprising engineered site-specific zinc fingers (with engineered recognition regions) fused to a nuclease domain. Such ZFNs have been successfully used for genome modification in a variety of different species. See, for example, United States Patent Publications 20030232410; 20050208489; 20050026157; 20050064474; 20060188987; 20060063231; and International Publication WO 07/014,275, the disclosures of which are incorporated by reference in their entireties for all purposes. These ZFNs can be used to create a double-strand break (DSB) in a target nucleotide sequence, which increases the frequency of donor nucleic acid introduction via homologous recombination at the targeted locus (targeted integration) more than 1000-fold. In addition, the inaccurate repair of a site-specific DSB by non-homologous end joining (NHEJ) can also result in gene disruption. Nucleases can be used for a wide variety of purposes such as for cell line engineering as well as for therapeutic applications.

Efficiency of nuclease activity can be influenced by a variety of factors such as accessibility of the target and the quality of the binding interaction between the nuclease and its target nucleic acid. To increase the success rate of nuclease driven genomic modifications, researchers often have to resort to introducing selectable markers during donor integration in order to be able to select variants that have had modifications from those that have not been modified (see, for example, U.S. Pat. No. 6,528,313). For a number of applications, use of selectable markers is not desirable as this technique leaves an additional gene or nucleic acid sequence inserted into the genome.

Thus, there remains a need for compositions and methods for increasing nuclease activity to allow for more efficient use of these powerful tools.

SUMMARY

Described herein are methods and compositions for increasing activity of an exogenous nuclease (e.g.; ZFN) in a host cell. The methods involve the use of transient hypothermia, i.e. "cold shock," to cells following transfection with the expression vectors encoding the nuclease. The cells are held at the reduced temperature for an extended period of time and then are shifted back to the appropriate temperature to recover and increase cell division, a method that can increase the rate of gene disruption by more than ten-fold. The methods and compositions may be used for targeted genomic modification through introduction of mutations via NHEJ, and also may be used for targeted donor nucleic acid insertion via homologous recombination. The methods and compositions described herein significantly increase the efficiency of nuclease activity in a host cell.

In one aspect, described herein is a method for increasing activity of an exogenous nuclease (e.g., in mammalian cells by subjecting the cells to cold shock following transfection, and, following the cold shock, returning the cells to an appropriate temperature for growth). In certain embodiments, the cold shock temperature is between 27 and 33° C. In certain embodiments, the cells are subjected to cold shock for between 1 and 4 days.

In another aspect, the invention provides a host cell comprising a nuclease expression plasmid wherein the host cell has been subject to a cold shock. In another aspect, the nuclease(s) is(are) delivered to the cell via Integration Defective Lentiviral (IDLV) constructs (see for example United States Patent Publication 2009/0117617, incorporated herein by reference) or by integration competent lentiviral vectors. In another aspect, the nuclease(s) is(are) delivered to the cell via an adenoviral vector or an adenoviral associated vector (AAV). In one aspect, the invention provides a mammalian host cell at 33° C. or lower comprising a nuclease (e.g., ZFN) expression plasmid and a donor nucleic acid such that the nuclease mediates targeted integration of the exogenous sequence into the genome. In certain embodiments, the cell is a eukaryotic cell (e.g., a mammalian cell). In some aspects, the host cells are an established cell line while in other aspects, the host cell is a primary cell isolated from a mammal. In some aspects, the invention provides a host cell as above wherein the donor nucleic acid encodes a reporter construct which may be transiently or stably expressed in the host cell. Any of the host cells may further comprise a sequence encoding a nuclease, for example a homing nuclease or zinc finger nuclease.

In another aspect, the invention provides a host cell comprising a donor nucleic acid wherein the donor nucleic acid has been integrated into the genome of the host cell using the methods provided herein. In certain embodiments, the cell is a eukaryotic cell (e.g., a mammalian cell). Any of the host cells may further comprise a sequence encoding a nuclease, for example a homing nuclease or zinc finger nuclease.

In yet another aspect, provided herein is a method of increasing the nuclease activity of a known nuclease, the method comprising the steps of: introducing one or more expression constructs that express the nuclease(s) into any of the host cells described herein, incubating the cells under cold shock conditions such that the nuclease is expressed but the rate of cell division is greatly reduced; and then culturing the cells in an appropriate temperature such that the rate of cell division increases, thereby increasing the nuclease activity of the known nuclease. In certain embodiments, the methods further comprise the step of determining the level of nuclease activity. In any of the methods described herein, the nuclease may comprise, for example, a non-naturally occurring DNA-binding domain (e.g., an engineered zinc finger protein, a TAL-effector nuclease fusion protein, or an engineered DNA-binding domain from a homing endonuclease). In certain embodiments, the nuclease is a zinc finger nuclease (ZFN) or pair of ZFNs. In other embodiments, the nuclease is a TAL-effector domain nuclease fusion protein.

Any of the methods may further comprise introducing an exogenous sequence into the host cell such that the nuclease mediates targeted integration of the exogenous sequence into the genome. In certain embodiments, the exogenous sequence is introduced at the same time as the nuclease(s). In some aspects, the exogenous sequence may comprise a reporter gene. In certain embodiments, the methods further comprising isolating the cells expressing the reporter gene. In any of the methods described herein, the genomic modification is a gene disruption and/or a gene addition.

Furthermore, in any of the methods described herein, the nuclease(s) (e.g., ZFN, ZFN pair, TAL-effector domain nuclease fusion protein, engineered homing endonuclease and/or fusion or a naturally occurring or engineered homing endonuclease. DNA-binding domain and heterologous cleavage domain) may be known to recognize the endogenous target sequence, for example from results obtained from in vitro assay experiments.

In another aspect, the invention provides kits that are useful for increasing the activity of nucleases (e.g. ZFNs, TAL-effector domain nuclease fusion proteins, or engineered homing endonucleases). The kits typically include one or more nucleases that bind to a target site, optional cells containing the target site(s) of the nuclease and instructions for introducing the nucleases into the cells and cold shocking the cells to increase nuclease activity. In certain embodiments, the kits comprise at least one construct with the target gene and a known nuclease capable of cleaving within the target gene. Such kits are useful for optimization of cleavage conditions in a variety of varying host cell types. Other kits contemplated by the invention may include a known nuclease capable of cleaving within a known target locus within a genome, and may additionally comprise a donor nucleic acid encoding a reporter gene. Such kits are useful for optimization of conditions for donor integration. In such kits, the reporter gene may be operatively linked to a polyadenylation signal and/or a regulatory element a promoter).

BRIEF DESCRIPTION OF THE DRAWINGS

(FIG. 2A) or 1 day at 37° C. followed by 2 days at 30° C. (FIG. 2B). The frequency of small insertions or deletions (indels) is shown beneath each lane. In all cases, cold shock treatment increased the ZFN activity, as determined by CEL-1 assay.

FIG. 3A shows the results of the CEL-I assay for NHEJ activity performed at the end of the 3 days and shows that ZFN activity was greatly increased when the cells were allowed to recover at 30° C. Following the initial 3 day incubation at either 30° C. or 37° C., cells were all placed at 37° C. for a period of an additional 21 days. Following this incubation at 37° C., cells were processed for the CEL-I assay as described above. FIG. 3B shows that the increased genome modification seen in the population of cells initially incubated at 30° C. is stable over an additional 7 days.

FIG. 4A shows the results of the CEL-I assay for NHEJ activity performed at the end of the 3 days and shows that ZFN activity was greatly increased when the cells were allowed to recover at 30° C. Following the initial 3 day incubation at either 30° C. or 37° C., cells were all placed at 37° C. for a period of an additional 7 days. Following this 7 day incubation at 37° C., cells were processed for the CEL-I assay as described above. FIG. 4B shows that the increased genome modification seen in the population of cells initially incubated at 30° c. is stable over 21 cell doublings under normal growth conditions (i.e. 37° C.). In particular, up to ~25% of the chromatids were modified in the cold shock-treated population as compared to 1% in cells incubated at 37° C.

FIGS. 5A and 5B show results of K652 cells nucleofected with a GFP expression plasmid (−) or 80 ng of a CMV promoter-driver ZFN expression vector (lanes 2-5 and 7-10) targeted to the GR gene containing either wild-type FokI cleavage domains or obligate heterodimer FokI cleavage domains. Immediately after transfection, cells were divided and incubated for 3 days at 37° C. (lanes 2-3 and 7-8) or 3 days at 30° C. (lanes 4-5 and 9-10). The heterodimeric variants (lanes 2-5) and wild-type FokI domain (lanes 7-10) were compared. The frequency of indels at the GR locus was assessed by CEL-1 assay 3 days post-transfection. FIGS. 5C and 5D show the frequency of indels in intron 1 of Trim26 (off-target) as assessed by CEL-1 assay 3 days post-transfection of the GR-targeted ZFNs described above. FIGS. 5E and 5F show the frequency of indels in intron 1 of chromosome 1 (off-target) as assessed by CEL-1 assay 3 days post-transfection of the GR-targeted ZFNs described above.

DETAILED DESCRIPTION

Figure 1:
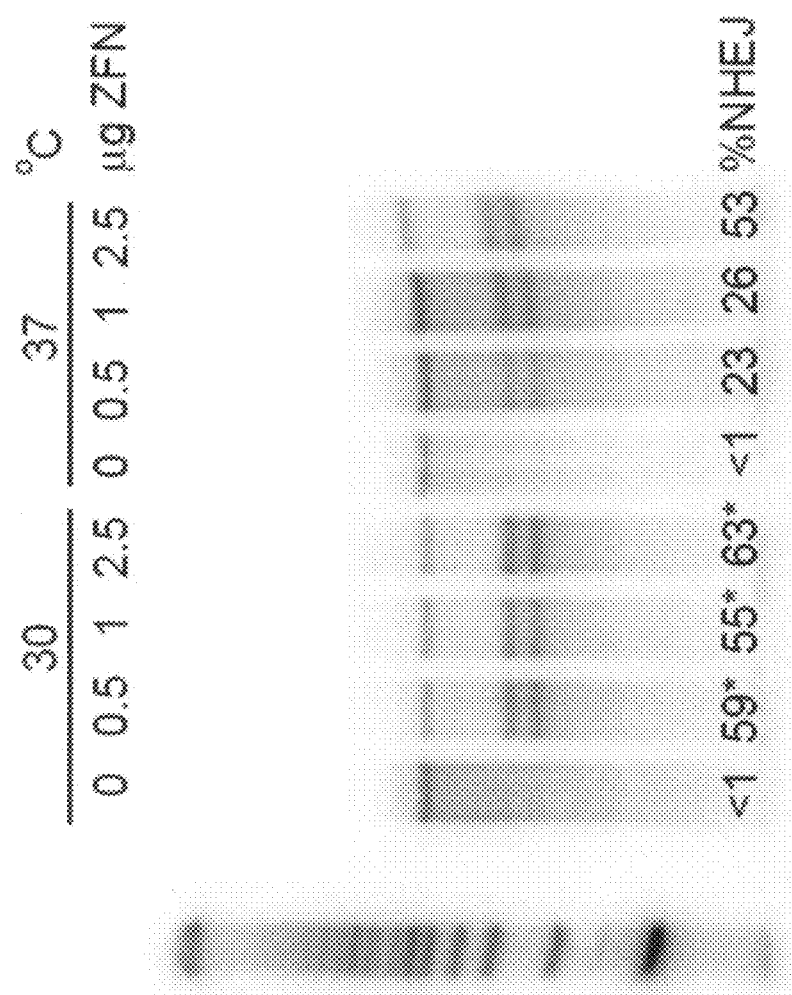
FIG. 1 shows a gel depicting a comparison of ZFN activity as determined by the CEL-I assay (SURVEYOR™, Transgenomic) at 30° C. versus 37° C. Varying amounts of AAVS1-specific ZFN expression plasmid were used: 0.5, 1 or 2.5 μg. K562 cells were transfected with the expression plasmid and then divided into two populations to recover at either 30° C. or 37° C. for 4 days. At that time, cells were processed for the CEL-I assay to detect any mismatches that have occurred due to NHEJ activity. The percent NHEJ activity is indicated at the bottom of each lane. The data demonstrate that the activity of the ZFNs is increased when the cells are held at 30° C. At observed NHEJ percentages greater than approximately 40%, the results from the CEL-I assay become non-linear. Thus NHEJ percentages greater than 40% are estimates and are indicated with an asterisk (*).

Described herein are compositions and methods to increase nuclease activity and kits comprising the methods described. In particular, the methods use transient hypothermia for varying length of times following host cell transfection with the nuclease expression plasmid(s). After the period of cold shock, the host cells are returned to a more appropriate temperature to allow the cells to initiate or increase cell division. In addition, the compositions and methods described herein can also be used to optimize nuclease cleavage conditions for gene disruption and/or gene addition in a variety of host cells.

Engineered nuclease technology is based on the engineering of naturally occurring DNA-binding proteins. For example, engineering of homing endonucleases with tailored DNA-binding specificities has been described. Chames et al. (2005) *Nucleic Acids Res* 33(20):e178; Arnould et al. (2006) *J. Mol. Biol.* 355:443-458. In addition, engineering of ZFPs has also been described. See, e.g., U.S. Pat. Nos. 6,534,261; 6,607,882; 6,824,978; 6,979,539; 6,933,113; 7,163,824; and 7,013,219.

In addition, ZFPs have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) *Proc Natl Acad Sci USA* 93(3):1156-1160. More recently, ZFNs have been used for genome modification in a variety of organisms. See, for example, United States Patent Publications 20030232410; 20050208489; 20050026157; 20050064474; 20060188987; 20060063231; and International Publication WO 07/014,275.

The biological activity of nucleases is not always the same from cell type to cell type. Thus, methods which can increase nuclease activity can be used to increase the success rate in a variety of cell types for either targeted gene disruption at a specified locus through nuclease-mediated NHEJ, or to increase the amount of gene addition/deletion through nuclease-mediated homologous recombination.

Thus, the methods and compositions described herein provide highly efficient and rapid methods for increasing biological activity of nucleases in vivo. The methods and compositions described herein also provide the components for kits to allow for optimization and characterization of nucleases within a cell.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains (e.g., the recognition helix region) can be "engineered" to bind to a predetermined nucleotide sequence. The engineered region of the zinc finger is typically the recognition helix, particularly the portion of the alpha-helical region numbered −1 to +6. Backbone sequences for an engineered recognition helix are known in the art. See, e.g., Miller et al. (2007) *Nat Biotechnol* 25, 778-785. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528 and 2008/0131962, incorporated herein by reference in their entireties.

"Cold shock" refers to a shift in temperature wherein cells are placed in a hypothermic environment that is colder than optimal growth temperature. The cold shock temperature will depend on the cell type, in particular the temperature that is optimal for cell division to occur in that cell type. For mammalian cells, cold shock temperatures will typically be, 33° C., 32° C., 31° C., 30° C., 29° C., and 28° C. or even lower. Zebrafish cell lines are grown at 28° C., so an optimal cold shock temperature would be lower than 28° C., for example, lower than 25° C., 24° C., 23° C., 22° C., or even lower. Similarly, plant protoplasts divide at cooler temperatures than mammalian cells, and so a suitable cold shock temperature would necessarily be cooler than that used for mammalian cells.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein; polysaccharide, any modified derivative of the above molecules, or any complex comprising one or more of the above molecules. Nucleic acids include DNA and RNA, can be single- or double-stranded; can be linear, branched or circular; and can, be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a, protein in a cell. Methods for polynucleotide and polypeptide delivery to cells are presented elsewhere in this disclosure.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

Overview

Described herein are compositions and methods for increasing the biological activity of nucleases within a cell. The compositions and methods described are effective in increasing nuclease activity in a variety of cell types wherein a desired genomic modification is needed. In the methods described herein, nucleic acids encoding a nuclease(s) specific for a desired target site(s) are introduced into a host cell. Following introduction of the nuclease-encoding nucleic acid, the cells are subject to a period of "cold shock" by placing the transfected cells in a hypothermic environment for a period of time. During the period of cold shock time, nucleases are expressed and are active but the ability of the host cells to divide is reduced or eliminated. Following the period of cold shock, the cells are returned to a temperature that increases the rate of cell division. The transient period of cold shock unexpectedly increases the efficiency of nuclease activity with a concomitant increase in either stimulated homologous recombination in the presence of a donor nucleic acid, or an increase in imprecise non-homologous end joining (NHEJ), without any observed deleterious effects.

Thus, described herein are rapid and efficient methods for increasing biological activity of nucleases. The methods have applications in a wide variety of cell types. Accordingly, the compositions and methods described herein can also be utilized in kits that allow the user to screen nucleases and to select cells with desired genomic modifications. The methods and compositions can also be used to facilitate the isolation of knock-out cell lines because the efficiency of nuclease digestion is greatly increased. This technology has application in the creation of cells and/or transgenic organisms that exhibit 'trait stacking' due to its ability to increase genome modification efficiency. The invention may also be used to increase the therapeutic applications of nucleases since it increases activity in a variety of cell types.

Host Cells

Any host cell wherein a genomic modification is desired may be used with the practice of the present disclosure. The cell types can be cell lines or natural (e.g., isolated) cells such as, for example, primary cells. Cell lines are available, for example from the American Type Culture Collection (ATCC), or can be generated by methods known in the art, as described for example in Freshney et al., Culture of Animal Cells, A Manual of Basic Technique, 3rd ed., 1994, and references cited therein. Similarly, cells can be isolated by methods known in the art. Other non-limiting examples of cell types include cells that have or are subject to pathologies, such as cancerous cells and transformed cells, pathogenically infected cells, stem cells, fully differentiated cells, partially differentiated cells, immortalized cells and the like. Prokaryotic (e.g., bacterial) or eukaryotic (e.g., yeast, plant, fungal, piscine and mammalian cells such as feline, canine, murine, bovine, porcine and human) cells can be used, with eukaryotic cells being preferred. Suitable mammalian cell lines include K562 cells, CHO (Chinese hamster ovary) cells, 293 cells, HEP-G2 cells, BaF-3 cells, Schneider cells, COS cells (monkey kidney cells expressing SV40 T-antigen), CV-1 cells, HuTu80 cells, NTERA2 cells, NB4 cells, HL-60 cells and HeLa cells, 293 cells (see, e.g., Graham et al. (1977) *J. Gen. Virol.* 36:59), and myeloma cells like SP2 or NS0 (see, e.g., Galfre and Milstein (1981) *Meth. Enzymol.* 73(B):3 46), rat C6 cells, and porcine Pk15 cells. Peripheral blood mononucleocytes (PBMCs) or T-cells can also serve as hosts. Additionally, suitable cells for use with the invention include stem cells such as primary stem cells as well as induced pluripotent stem cells. Other eukaryotic cells include, for example, insect (e.g., sp. *frugiperda*), fungal cells, including yeast (e.g., *S. cerevisiae, S. pombe, P. pastoris, K. lactis, H. polymorpha*), and plant cells (Fleer, R. (1992) *Current Opinion in Biotechnology* 3:486 496).

Nucleases

The methods and compositions described herein are broadly applicable and may involve any nuclease of interest. Non-limiting examples of nucleases include meganucleases, TAL effector nuclease domain fusion proteins, and zinc finger nucleases. The nuclease may comprise heterologous DNA-binding and cleavage domains (e.g., zinc finger nucleases; TAL-effector nuclease domain fusion proteins, meganuclease DNA-binding domains with heterologous cleavage domains) or, alternatively, the DNA-binding domain of a naturally-occurring nuclease may be altered to bind to a selected target site (e.g., a meganuclease that has been engineered to bind to site different than the cognate binding site).

In certain embodiments, the nuclease is a meganuclease (homing endonuclease). Naturally-occurring meganucleases recognize 15-40 base-pair cleavage sites and are commonly grouped into four families: the LAGLIDADG family ("LAGLIDADG" disclosed as SEQ ID NO: 11), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al: (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

DNA-binding domains from naturally-occurring meganucleases, primarily from the LAGLIDADG family ("LAGLIDADG" disclosed as SEQ ID NO: 11), have been used to promote site-specific genome modification in plants, yeast, Drosophila, mammalian cells and mice, but this approach has been limited to the modification of either homologous genes that conserve the meganuclease recognition sequence (Monet et al. (1999), Biochem. Biophysics. Res. Common. 255: 88-93) or to pre-engineered genomes into which a recognition sequence has been introduced (Route et al. (1994), Mol. Cell. Biol. 14: 8096-106; Chilton et al. (2003), Plant Physiology. 133: 956-65; Puchta et al. (1996), Proc. Natl. Acad. Sci. USA 93: 5055-60; Rong et al. (2002), Genes Dev. 16: 1568-81; Gouble et al. (2006), J. Gene Med. 8(5):616-622). Accordingly, attempts have been made to engineer meganucleases to exhibit novel binding specificity at medically or biotechnologically relevant sites (Porteus et al. (2005), Nat. Biotechnol. 23: 967-73; Sussman et al. (2004), J. Mol. Biol. 342: 31-41; Epinat et al. (2003), Nucleic Acids Res. 31: 2952-62; Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication Nos. 20070117128; 20060206949; 20060153826; 20060078552; and 20040002092). In addition, naturally-occurring or engineered DNA-binding domains from meganucleases have also been operably linked with a cleavage domain from a heterologous nuclease (e.g., FokI).

In some embodiments, the nuclease is a TAL-effector domain fusion protein, where the TAL effector domain is a natural or engineered TAL effector domain fused to a nuclease domain (e.g. FokI). See co-owned U.S. Patent Application No. 61/395,836 for Novel DNA-binding proteins and uses thereof, filed May 17, 2010.

In other embodiments, the nuclease is a zinc finger nuclease (ZFN). ZFNs comprise a zinc finger protein that has been engineered to bind to a target site in a gene of choice and cleavage domain or a cleavage half-domain.

Zinc finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789, 538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; ZFNs and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, zinc finger domains and/or multi-fingered zinc finger proteins may be linked together using any suitable linker sequences, including for example, linkers of 5 or more amino acids in length. See, e.g., U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Nucleases such as ZFNs, TAL-effector domain nuclease fusions, and/or meganucleases also comprise a nuclease (cleavage domain, cleavage half-domain). As noted above, the cleavage domain may be heterologous to the DNA-binding domain, for example a zinc finger DNA-binding domain and a cleavage domain from a nuclease or a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases, Cold Spring Harbor Laboratory Press,* 1993). One or more of these enzymes (or functional fragments thereof) can be used as a source of cleavage domains and cleavage half-domains.

Similarly, a cleavage half-domain can be derived from any nuclease or portion thereof, as set forth above; that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the FokI enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014,275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474 and 20060188987 and in U.S. application Ser. No. 11/805,850 (filed May 23, 2007), the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes.

The engineered cleavage half-domains described herein are obligate heterodimer mutants in which aberrant cleavage is minimized or abolished. See, e.g., Example 1 of WO 07/139,898. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See U.S. provisional application 61/337,769 filed Feb. 8, 2010).

Engineered cleavage half-domains described herein can be prepared using any suitable method, for example, by site-directed mutagenesis of wild-type cleavage half-domains (Fok I) as described in U.S. Patent Publication Nos. 20050064474 and 20080131962.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases (e.g., ZFNs) can be screened for activity prior to use, for example in a yeast-based chromosomal system as described in WO 2009/042163 and 20090068164.

Nuclease expression constructs can be readily designed using methods known in the art. See, e.g., United States Patent Publications 20030232410; 20050208489; 20050026157; 20050064474; 20060188987; 20060063231; and International Publication WO 07/014,275. Expression of the nuclease may be under the control of a constitutive promoter or an inducible promoter, for example the galactokinase promoter which is activated (de-repressed) in the presence of raffinose and/or galactose and repressed in presence of glucose.

Cold Shock Conditions

The methods described herein involve subjecting the host cells to a period of cold shock before, during or after introduction of the nuclease(s) and/or donor polynucleotide. Typically, the cells are cold-shocked following introduction of (e.g., transfection with) the nuclease and/or donor nucleotide. The cells may be cold-shocked within minutes after transfection or may be maintained at 37° C. for a short period of time (1 day for example) prior to shifting to the cooler temperature.

The period of time for which the cells are cold shocked can vary from hours to days. In certain embodiments, the cells are cold-shocked for between 1 and 4 days. It will be apparent that the period of cold shock will also vary depending on the cell type into which the nuclease is introduced.

Likewise, the temperature at which the cells are cold-shocked is any temperature that reduces cell division, but at which the nuclease(s) is (are) expressed and/or active. Suitable temperatures will vary depending on the host cell type. For mammalian cells, cold shock temperatures include, but are not limited to, 33° C., 32° C., 31° C., 30° C., 29° C., 28° C., 27° C., and even lower. For zebrafish and plant cells, the cold shock temperatures will typically be lower, for example 26° C., 25° C., 24° C., 23° C., 22° C., 21° C., 20° C., 19° C., 18° C. or event lower. Furthermore, the temperature can vary during the period of cold-shocking, so long as it remains low enough so that the cells are not dividing or are dividing at a reduced rate.

Kits

Also provided are kits for performing any of the above methods. The kits typically contain polynucleotides encoding one or more nucleases and/or donor polynucleotides as described herein as well as instructions for cold-shocking the cells into which the nucleases and/or donor polynucleotide are introduced. The kits can also contain cells, buffers for transformation of cells, culture media for cells, and/or buffers for performing assays. Typically, the kits also contain a label which includes any material such as instructions, packaging or advertising leaflet that is attached to or otherwise accompanies the other components of the kit.

Applications

The disclosed methods and compositions can be used for increasing biological activity of nucleases on their targets in the genome of any host cell. Typically, the host cells are first transfected with an expression construct that directs expression of one or more nucleases within the cell. Following transfection, the cells are placed in a cold shock condition that allows for expression of the nucleases but in which the rate of cell division is reduced. Following the period of cold shock, the cells are returned to a temperature suitable for increased cell division. Under these conditions, the efficiency of gene disruption is greatly increased, and, accordingly, the methods described herein allow for the rapid generation of knock out cell lines (cells in which one or more genes have been deleted ("knocked out") or disrupted). Similarly, the methods described herein facilitate the generation of cell lines wherein one or more genes or nucleic acids have been introduced into the genome.

In addition, the compositions and methods described herein allow for efficient generation of primary cells containing nuclease-modified genomes. Nuclease-modified cells may be used in therapeutic applications, for example by deleting a receptor for a virus (see United States Publication 20080159996) or for a growth factor (see United States Publication 20080188000). Such cells may be then re-introduced into a mammal to carry out a therapeutic effect.

Further, the methods and compositions described herein may be used in plant cells. Plant cells carrying genomic modifications created by the contemplated methods and compositions may be used to regenerate whole plants and create novel plant lines. Increasing nuclease activity may lead to increased ability to generate plant lines with multiple introduced desired traits (i.e. trait stacking).

Additionally, methods and compositions described herein may be used in the construction of transgenic animals. Genomic modifications (via NHEJ or additions and/or deletions) may be introduced in embryos, and then these genomically modified embryos may be used to create transgenic animals using any known suitable method.

Methods and compositions described herein are also used in kits suitable for the optimization of nucleases as well as for targeted nucleic acid insertion or deletion into the genome of a cell.

The following Examples relate to exemplary embodiments of the present disclosure in which the nuclease comprises a zinc finger nuclease (ZFN). It will be appreciated that this is for purposes of exemplification only and that other nucleases can be used, for instance homing endonucleases (meganucleases) with engineered DNA-binding domains and/or fusions of naturally occurring engineered homing endonucleases (meganucleases) DNA-binding domains and heterologous cleavage domains or TAL-effector domain nuclease fusion proteins.

EXAMPLES

Example 1

Preparation of ZFNs

ZFNs targeted to the various genes used in this study were designed and incorporated into plasmids or adenoviral vectors essentially as described in Urnov et al. (2005) *Nature* 435(7042):646-651, Perez et al (2008) *Nature Biotechnology* 26(7): 808-816, and U.S. Patent Publication 20080299580: Zinc finger proteins were designed as described in co-owned U.S. Pat. Nos. 6,453,242 and 6,534,261. See Table 1 for the amino acid sequences of the recognition regions of the AAVS1 zinc finger proteins and Table 2 for the sequences of the target sites. Sequences encoding each of these two ZFP binding domains were fused to sequences encoding a FokI cleavage half-domain (amino acids 384-579 of the native FokI sequence; Kita et al. (1989) *J. Biol. Chem.* 264:5751-5756), such that the encoded protein contained FokI sequences at the carboxy terminus and ZFP sequences at the amino terminus.

TABLE 1

Zinc Finger helices used

| Gene/ZFN name | F1 | F2 | F3 | F4 |
|---|---|---|---|---|
| AAVS1/ 15590 | QSSNLAR (SEQ ID NO: 1) | RTDYLVD (SEQ ID NO: 2) | YNTHLTR (SEQ ID NO: 3) | QGYNLAG (SEQ ID NO: 4) |
| AAVS1/ 15556 | YNWHLQR (SEQ ID NO: 5) | RSDHLTT (SEQ ID NO: 6) | HNYARDC (SEQ ID NO: 7) | QNSTRIG (SEQ ID NO: 8) |

Note:
The zinc finger amino acid sequences shown above (in one-letter code) represent residues −1 through +6, with respect to the start of the alpha-helical portion of each zinc finger. Finger F1 is closest to the amino terminus of the protein, and Finger F4 is closest to the carboxy terminus.

TABLE 2

ZFN Target sequences

| Gene/ZFN name | Target Site |
|---|---|
| AAVS1/ 15590 | acTAGGGACAGGATtg (SEQ ID NO: 9) |
| AAVS1/ 15556 | ccCCACTGTGGGGTgg (SEQ ID NO: 10) |

Additional ZFNs targeted to the following genes were also obtained from Sigma-Aldrich: KDR, TP73, MAP3K14, EP300, BTK135, CARM1, GNAI2, TSC2, RIPK1, and KDR. GR-targeted ZFNs were prepared as described above and in U.S. Patent Publication No. 2008/0188000.

Example 2

Increased Nuclease Activity Following Cold Shock

ZFN activity was increased several fold when cells were treated with a cold shock condition following transfection. Briefly, the plasmid encoding ZFP-FokI fusions were introduced into K562 cells by transfection using the Amaxa™ Nucleofection kit as specified by the manufacturer. For transfection, two million K562 cells were mixed with varying amounts of each zinc-finger nuclease expression plasmid and 100 µL Amaxa Solution V. Cells were transfected in an Amaxa Nucleofector II™ using program T-16. Immediately following transfection, the cells were divided into two different flasks and grown in RPMI medium (Invitrogen) supplemented with 10% FBS in 5% $CO_2$ at either 30° C. or 37° C. for four days. To determine the ZFN activity at the appropriate locus (e.g., AAVS1 locus for AAVS1 targeted ZFPs), CEL-I mismatch assays were performed essentially as per the manufacturer's instructions (Trangenomic SURVEYOR™).

Cells were harvested and chromosomal DNA prepared using a Quickextract™ Kit according to manufacturer's directions (Epicentre®). The appropriate region of the target locus was PCR amplified using Accuprime™ High-fidelity DNA polymerase (Invitrogen). PCR reactions were heated to 94° C., and gradually cooled to room temperature. Approximately 200 ng of the annealed DNA was mixed with 0.33 µL CEL-I enzyme and incubated for 20 minutes at 42° C. Reaction products were analyzed by polyacrylamide gel electrophoresis in 1× Tris-borate-EDTA buffer.

Nuclease activity, as measured by CEL-I detection of NHEJ activity, increased in the cells that had been incubated at 30° C. FIG. 1A shows results using AAVS1-targeted ZFNs. Control lanes from experiments using 0 µg of ZFN expression plasmid showed no mismatches, while the experiment that used 0.5 µg ZFN expression plasmid showed a large increase in the percent of modification. The same was true for experiments using 1 and 2.5 µg of input ZFN expression plasmid. Furthermore, at 30° C. cold-shock incubation, all results were in the non-linear range of detection (above approximately 40% mismatch, as denoted by an *), indicating that the assay was saturated at this high of a percentage of mismatch.

Figure 2:
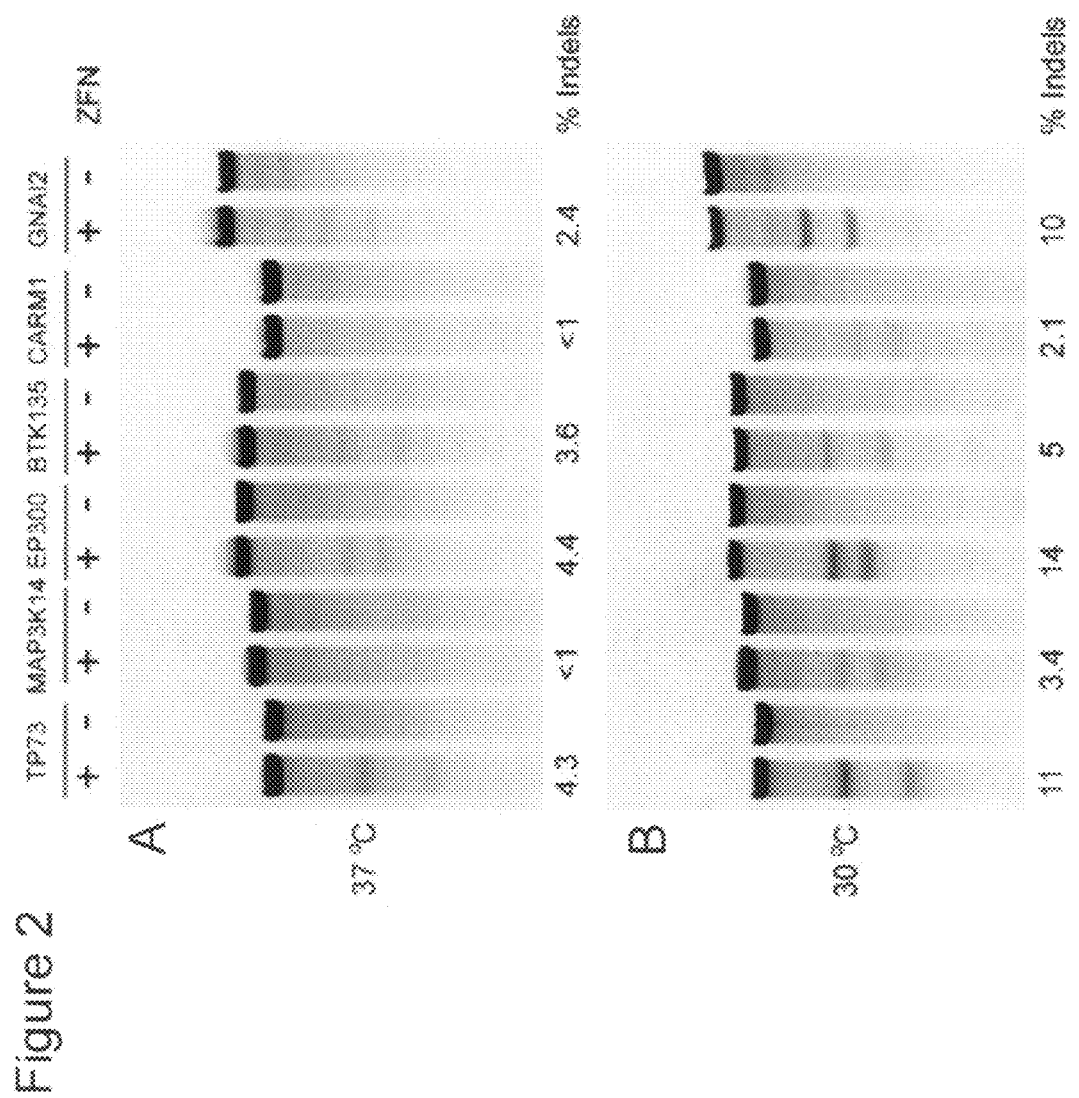
FIG. 2, panels A and B, depict the effect of cold shock on the six different ZFNs indicated at the top of each lane. K562 cells were transfected with 0.4 μg of the indicated ZFN expression vector and incubated for 3 days at 37° C.

FIG. 2 shows results using MAP3K14, EP300, BTK, CARM1 and GNAI2-targeted ZFNs. In all cases, cold shock conditions (FIG. 2B) enhanced. ZFN activity (2 to 10 fold or more) as compared to no cold shock (FIG. 2C), as measured by the increased frequency of genomic modifications following ZFN cleavage. Importantly, ZFNs pairs (MAP3K14 and CARM1) for which activity was not detected at 37° C. were sufficiently active following cold shock to provoke a robust gene disruption signal (FIG. 2B).

Cold shock treatment also increased ZFN activity for all ZFNs tested at sub-maximal DNA vector doses, with the increase in CEL-I signal demonstrating stability over time in culture.

In addition, ZFN protein level and activity under normal and cold shock conditions was also determined. Using ZFNs targeting the KDR gene, a dose-dependent and stable augmentation in CEL-I signal with increasing vector concentration, an effect enhanced by the use of an intron containing vector at 37° C. Western blotting revealed a marked increase in the steady state level of ZFN protein under all cold shock conditions tested, an effect that paralleled the improvement in gene disruption efficiency in both HeLa and K562 cells. Thus, the increase in ZFN activity obtained via a transient cold shock results, at least in part, from the accumulation of ZFN protein.

Example 3

Increase in ZFN Activity is not Cell Type Specific and Modifications are Stable Over Time To examine if the increase in ZFN activity could be observed for more than one cell type, the experiments were repeated with HeLa cells. Cells were transfected with 0.1, 0.2 or 0.4 µg of AAVS1-specific ZFNs using the 96-well Nucleofector® Kit SE as per manufacturer recommendations. In addition, cells were incubated for 3 days following transfection at the 30° C. or 37° C. incubation temperatures.

Figure 3:
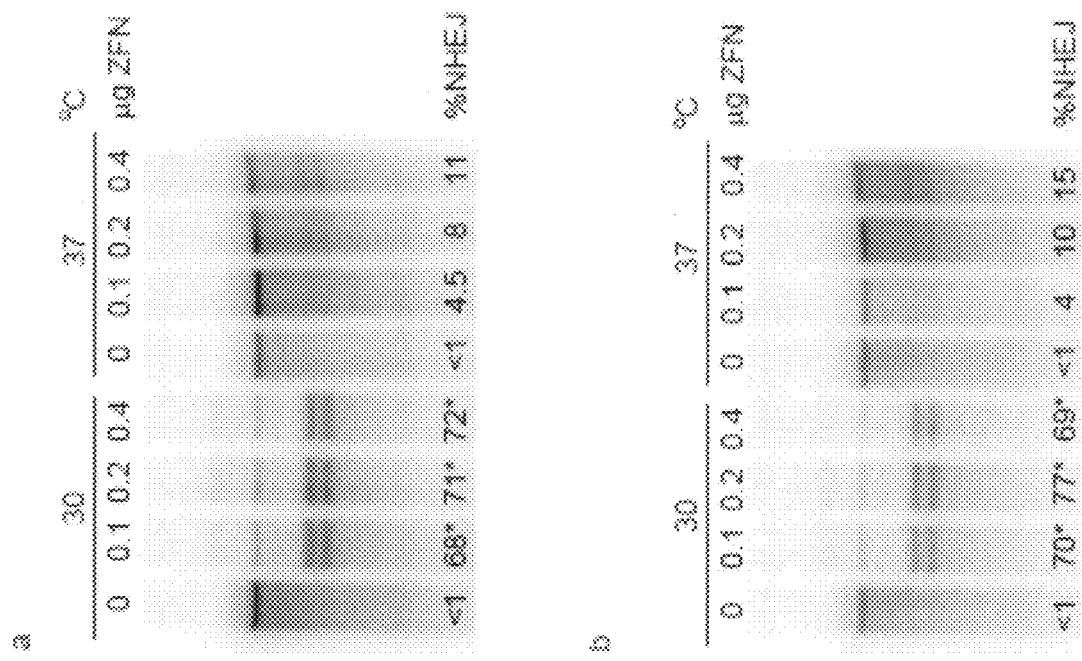
FIG. 3, panels A and B, are gels depicting CEL-I assay results of HeLa cells transfected with nucleases at 30° C. or 37° C. Cells were transfected with 0.1, 0.2 and 0.4 μg of ZFN expression construct encoding AAVS1-specific ZFNs, and, following transfection were divided into two populations and allowed to recover at either 30° C. or 37° C. for 3 days.

As shown in FIG. 3A, control experiments without added ZFN expression plasmid (lane labeled "0") did not exhibit any mismatches while cells transfected with 0.1, 0.2 or 0.4 µg of expression plasmid did. Again, large increases in nuclease activity were seen in the cells incubated at 30° C. as compared to those incubated at 37° C. As was seen in Example 2, the NHEJ values determined for those cells incubated at 30° C. were in the non-linear range of the assay (indicated by *) as the assay became oversaturated. Similarly, FIG. 4A shows an increase in ZFN activity following cold shock using a KDR-targeted ZFN (Sigma-Aldrich).

To determine if the modifications are stable over time, a portion of populations of the cells were maintained at 37° C. or 30° C. for an additional cell doublings. Following additional time in culture, cells were then processed for the CEL-I assay as above.

Figure 4:
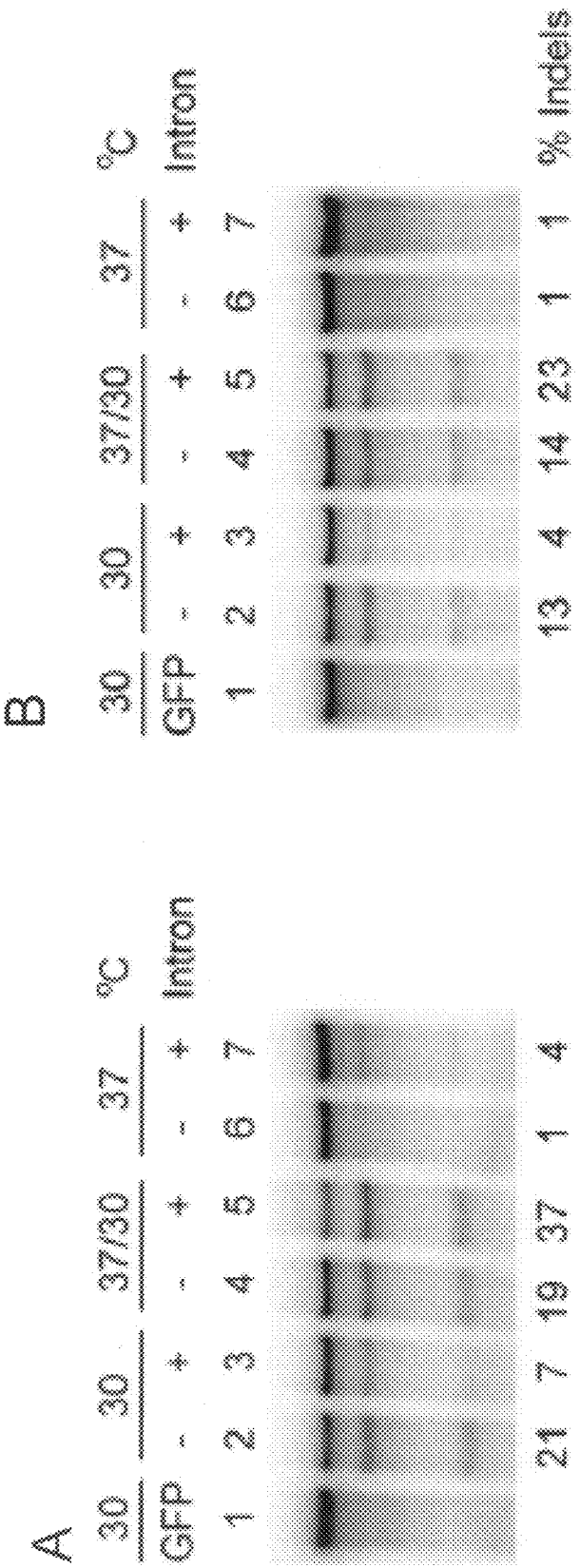
FIG. 4, panels A and B, are gels depicting CEL-I assay results of HeLa cells transfected with KDR-targeted nucleases at 30° C. or 37° C. Cells were transfected with 0.1, 0.2 and 0.4 μg of ZFN expression plasmid, and, following transfection were divided into two populations and allowed to recover at either 30° C. or 37° C. for 3 days.

Exemplary results are shown in FIGS. 3B and 4B. The data indicates that the amount of measured nuclease activity, as assayed by NHEJ activity, is very similar to that measured following the initial incubation period. Thus, the increase in genomic modification due to increased nuclease activity is not lost during the 37° C. incubation following the initial 30° C. incubation.

Example 4

Summary of Data Obtained from Numerous Cell Types

The method as described above was repeated with several different cell types, using varying methods of transfection and various ZFNs. Details about the transfection methods used are as follows. For transfection of ZFN expression plasmids via electroporation, the methodology used was essentially as above. For transduction of cells with a lentiviral based ZFN expression vector, the methodology used was as described in Lombardo et al, (2007) *Nature Biotechnology* vol 25 (11): 1209-1306.

In this survey analysis, two different types of nuclease domains in the ZFNs were used as well, the wild type domain (wt) as well as the obligate heterodimeric domain ('HiFi'). Cell types used were from human, mouse, rat hamster and pig origins. As is seen in Table 3 below, the increase in nuclease activity observed from the 30° C. treatment varied from a 1.5 to a 15-fold increase in activity as compared to 37° C. alone. In all cases shown, the cells received a 3 day 30° C. cold shock prior to analysis. Overall, the largest increases in nuclease activity were observed in ZFN with the lowest amounts of activity and with the ZFNs wherein the nuclease domain was of the obligate heterodimeric type.

TABLE 3

Summary of cell lines tested for ZFN activity under cold shock conditions

| Species | Cell type | Fold effect | # ZFN pairs tested | FokI domain | Transfection method |
| --- | --- | --- | --- | --- | --- |
| Human | K562 | 1.5*-5x | 7 | wt, HiFi | electroporation |
| Human | Hela | 2->15x | 7 | HiFi | electroporation |
| Human | HEK 293 | 1.5*-15x | 4 | wt, HiFi | lipofection electroporation |
| Mouse | Splenocytes | 2x | 1 | wt, HiFi | electroporation |
| Rat | C6 | 4x | 1 | HiFi | lentivirus |
| Hamster | CHO-K1 | 1.5†-2*x | 3 | wt, HiFi | electroporation |
| Pig | PK15 | 3-12x | 4 | HiFi | electroporation |

*These ZFN produce >15% NHEJ at 37° C.
†These ZFN produce >20% NHEJ at 37° C.

Thus, cold shock resulted in similar improvements in primary cells as well as transformed lines derived from a variety of species, independent of the ZFN pair or delivery method.

In addition, nuclease activity was also tested following different periods of cold shock (e.g., 2 days, 3 days). While cold shock conditions increased nuclease activity, optimal treatment duration varied among cell lines.

Example 5

Preferentially Cleavage of Target Sequences Under Cold Shock Conditions

To determine whether increased ZFN protein levels alter specificity, the ratio was between on-target and off-target cleavage for a human glucocorticoid receptor gene (GR) targeted ZFN for which two off-target cleavage sites were known in K562 cells (both in non-coding regions of the genome) was determined as described above by CEL-1 assay. In particular, K652 cells were nucleofected with a GFP expression plasmid (−) or 80 ng of a CMV promoter-driver ZFN expression vector (lanes 2-5 and 7-10) targeted to the GR gene containing either wild-type FokI cleavage domains or obligate heterodimer FokI cleavage domains. Immediately after transfection, cells were divided and incubated for 3 days at 37° C. or 3 days at 30° C. The frequency of indels at the GR locus as well as off-target sites Trim26 and chromosome 1 were assessed by CEL-1 assay 3 days post-transfection.

Figure 5:
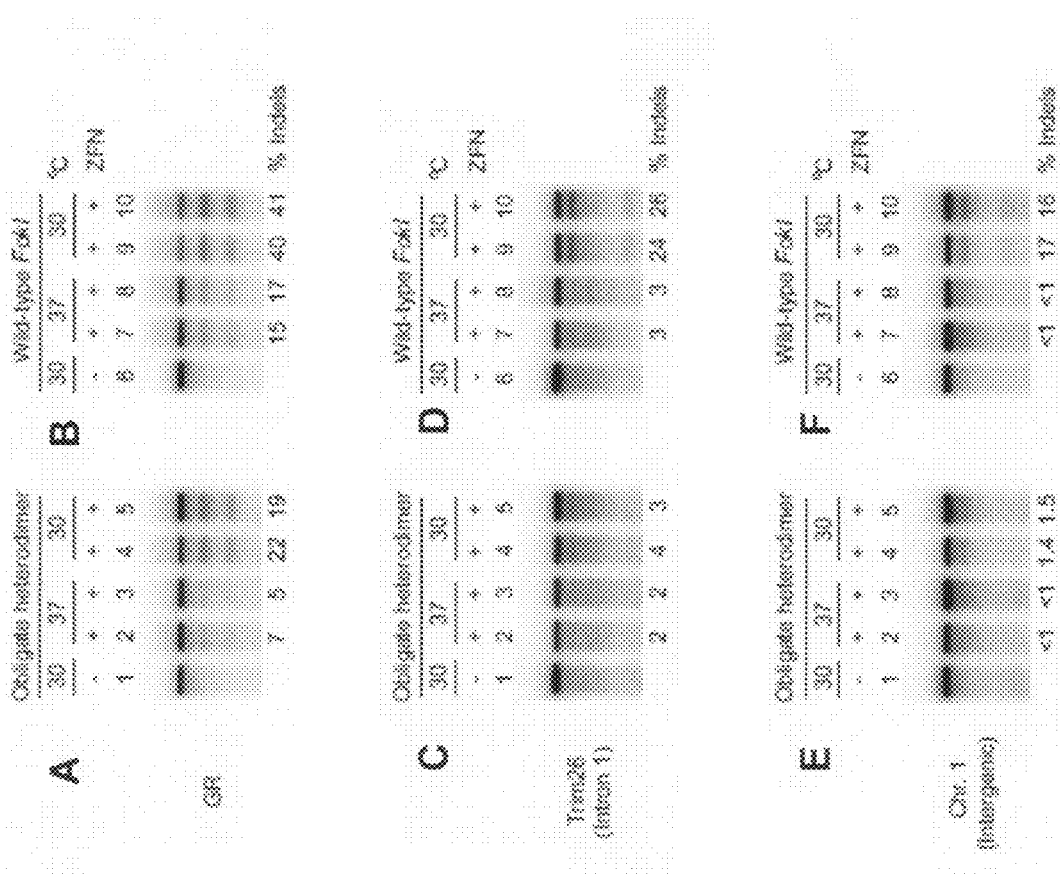
FIG. 5, panels A and F, show preferential cleavage of the ZFN target site under cold shock conditions.

As shown in FIG. 5, higher levels of ZFN protein (via cold shock) resulted in a proportional increase in ZFN activity at the intended (GR) and both off-target sites (FIG. 5). In contrast, the increase in off-target modification was markedly lower, yet on-target modification very high, when obligate heterodimer Fold variants were used. These data show that cold shock conditions can increase both activity and specificity of nucleases.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method for increasing the nuclease activity of at least one zinc finger nuclease in an isolated mammalian cell, the method comprising:

(a) culturing the isolated mammalian cell at an optimal growth temperature above 33° C.;

(b) transfecting the isolated mammalian cell with a polynucleotide encoding the at least one zinc finger nuclease (ZFN) into the isolated mammalian cell from step (a);

(c) culturing the isolated mammalian cell from step (b) at a temperature between 27° C. and 33° C. for between 1 and 4 days; and (d) culturing the isolated mammalian cell following step (c) at the optimal growth temperature, such that the nuclease activity of the ZFN is increased as compared to an isolated mammalian cell transfected and cultured only at the optimal growth temperature without the culturing step (c).

2. The method of claim 1, wherein the polynucleotide is transfected into the isolated mammalian cell using a viral vector, a plasmid or an RNA.

3. The method of claim 2, wherein the viral vector is an Integration Defective Lentiviral vector (IDLV) construct.

4. The method of claim 1, further comprising introducing an exogenous donor nucleic acid sequence into the isolated mammalian cell, wherein the isolated mammalian cell comprises a genome and the exogenous donor nucleic acid sequence is integrated into the genome of the isolated mammalian cell.

* * * * *

SEQUENCE LISTING

<160> NUMBER OF SEQ ID NOS: 11

<210> SEQ ID NO 1
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Ser Ser Asn Leu Ala Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Thr Asp Tyr Leu Val Asp
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Asn Thr His Leu Thr Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Gly Tyr Asn Leu Ala Gly
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Asn Trp His Leu Gln Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 6

Arg Ser Asp His Leu Thr Thr
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His Asn Tyr Ala Arg Asp Cys
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Asn Ser Thr Arg Ile Gly
1               5

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
actagggaca ggattg                                                         16

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ccccactgtg gggtgg                                                         16

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Ala Gly Leu Ile Asp Ala Asp Gly
1               5
```